United States Patent [19]

Faccioli et al.

[11] Patent Number: 5,004,501
[45] Date of Patent: Apr. 2, 1991

[54] TWO PHASE CEMENT MIXTURE, PARTICULARLY SUITABLE FOR OTHOPAEDICS

[75] Inventors: Giovanni Faccioli, Monzambano; Basilio M. De Bastiani, Montegrotto; Bruno Magnan, Verona; Renzo Soffiatti, Nogara, all of Italy

[73] Assignee: Tecres Spa, Bussolengo, Italy

[21] Appl. No.: 352,569

[22] Filed: May 16, 1989

[30] Foreign Application Priority Data

Jun. 1, 1988 [IT] Italy ............................... 84950 A/88

[51] Int. Cl.$^5$ ........................... C09K 3/00; A61F 5/04; A61F 2/00; C08K 3/00
[52] U.S. Cl. ...................................... 106/35; 524/401; 524/415; 524/428; 524/436; 524/438; 524/522; 524/523; 523/116; 523/117; 606/92
[58] Field of Search ................... 128/92 YQ; 524/401, 524/415, 428, 436, 438, 522, 523; 523/116, 117; 106/35

[56] References Cited

U.S. PATENT DOCUMENTS

| | | | |
|---|---|---|---|
| 3,856,737 | 12/1974 | Foster et al. | 524/433 |
| 3,962,267 | 6/1976 | Suzuki et al. | 524/433 |
| 4,718,910 | 1/1988 | Draenert | 523/116 |
| 4,791,150 | 12/1988 | Braden et al. | 523/116 |

*Primary Examiner*—Kriellion Morgan
*Attorney, Agent, or Firm*—Ladas & Parry

[57] ABSTRACT

The invention relates to a two phase cement mixture which is particularly suitable for orthopaedic use, in which the solid phase comprises a polymer, polymetyl methacrylate, and a catalyst, benzoyl peroxide, while the liquid phase comprises a monomer, monomethyl methacrylate, an accelerator, N-N-dimethyl-p-toluidine and hydroquinone. The said polymetyl methacrylate is in powder form with particles of a spherical shape which are of a suitable particle size. Fluoride in form of salt can be added to the said solid phase, realizing fluoride ions, making them available to the part of the bone with which the said mixture is in contact when is used to attach a prothesis to a bone.

5 Claims, No Drawings

TWO PHASE CEMENT MIXTURE, PARTICULARLY SUITABLE FOR OTHOPAEDICS

The invention relates to a two phase cement mixture which is particularly suitable for orthopaedic uses, having a solid phase comprising predominantly polymers and a liquid phase comprising predominantly monomer. The said phases are then joined together at the time of use to form a resin of plastic consistency which hardens in the course of time.

The said mixture, commonly known as bone cement, is known for use in orthopaedic surgery to provide a firm attachment for prostheses of various types to a variety of points on the uman skeleton. The term "cement" may incorrectly suggest an adhesive. In fact its function is instead to fill the spaces existing between the prosthesis, which is generally of metal, and the cavity in the bone prepared for its implantation.

This filling effect, associated with minimum physical expansion of the resin during polymerisation, provides a mechanical anchorage and a perfect fit between the implant and the bone. The best known use of this bone cement, to which we will refer without thereby restricting the scope of the invention, is that associated with the application of hip prostheses.

This surgical technique will now be described in principle in order that the invention may be better understood.

Once the need to replace the head of the femur with a prosthesis has been diagnosed, access is gained to the head by surgery and it is exposed so that it can be resected. The bone cavity is then bored out so that the cavity fits the shape of the prosthesis.

The cement is then prepared by combining the liquid phase with the solid phase and mixing the two until a plastic past is obtained. The cement so obtained is placed in the bone cavity and while it is still plastic the prosthesis is embedded in it and positioned accurately. There then is a wait of ten to fifteen minutes for the cement to harden and the femur is then repositioned with the new head in the correct position.

A similar procedure is used to position a cup prosthesis attached to the joint component of the pelvis. The cup made surgically is then closed completing the operation.

Because the orthopaedic cement is placed in direct contact with bone tissue, the chemical composition of the latter will now be described.

Bone tissue has two components: an inorganic component, also known as the mineral component, which forms the rigid framework of the tissue, and an organic component, also known as the biological component, which represents the "living" part of the structure.

The mineral component consists of calcium hydroxyapatite which precipitates in the tissue in the form of crystals, followed by a biochemical reaction which takes place in the organic matrix of the tissue under particular environmental conditions (pH, concentration, etc.) and in the presence of enzymes.

The organic component of the structure can be regarded as a connective tissue, that is a set of active cells specialised to a greater or lesser extent immersed in a matrix produced by the cells themselves. It is in this matrix, which is produced by the osteoblasts, i.e. the cells which specialise in the formation of the bone tissue, that the mineral crystals which give rise to the hydroxyapatite precipitate.

Wthen it is mature the bone tissue constructed in this way is organised into sheets which can form bony trabeculae or more compact bone tissue, also known as cortical tissue.

The cells contained within the metabolically stationary bony tissue are the osteocytes, while the cells responsable for the destruction and reabsorption of the tissue are the osteoclasts.

Both the osteoblasts and the osteoclasts are metabolically active cells and are subject to many controls of both a physiological and an artificially induced nature, the latter being of the chemical, biological or physical type transmitted to the above-mentioned cells by chemical substances such as hormones or drugs, or by physical stresses of the either a mechanical or electrical or electromagnetic type. It has been found clinically following orthopaedic implant prostheses cemented with acrylic resins that the use of known bone cements has the following disadvantages.

In a certain number of cases detachment or aseptic mobilisation of the implant occurs after a variable period of time.

This phenomenon is the most important complication of this surgical technique and is undoubtedly the factor which determines the result of the entire operation.

This detachment takes place at the bone-cement interface and take form of localised reabsorption of the bone tissue around the implant, with the replacement of this tissue by a reactive fibrous tissue, which may even be some thickness, which gives rise to mobilisation of the implant.

World literature attributes a primary role in the mechanism giving rise to detachment to the high temperature reached by the paste when it is hardenig as a result of the exothermic reactions produced by polymerisation. The temperature reached by the paste during the polymerisation varies, in clinical use, from 70° to 90° depending on the cement used, as described by B. Mjoberg, A. Rydholm et al. in the paper "low versus high viscosity bone cement" published in Acta Ortop Scand. 58, 106–108 in 1987.

The paste at high temperature in contact with the internal bone surface of the cavity produces scalding of the bone tissue which in turn gives rise to the formation of a necrotic-fibrous membrane consisting of dead cells which completely surrounds the cement mass introduced into the bone.

This membrane increases continually with the passage of time.

Following repeated stressing of the prosthesis caused by the load transferred to it, this membrane is compressed and flattened thus giving rise to play between the cement-prosthesis implant and the bone. This play allows the cemented prosthesis an increasing amount of the movement which initiates and amplifies wear of the material until the reconstructed joint fails.

In such cases cardio-respiratory depression due to the excessive amount of the liquid monomer coming into contact with the bone tissue occurs immeediatly after the cement is introduced into the bone cavity.

This depression makes it necessary to administer suitable drugs to the patient while still undergoing surgery in order to avoid possible cardio-respiratory collapse. This effect can be reduced somewhat by reducing the amount of the liquid monomer which is needed to form the correct paste.

The use of fluoride salts in osteoporotic syndromes, that is pathological rarefaction of the bone structure is based on observations made by Dr. Rotholm on workers occupationally exposed to the inhalatio or ingestion of large amounts of fluorine compounds.

The mechanisms of the action of the fluorides on bone tissue can be controlled and reproduced, as shown in work by various authors in the review "Fluoride in medicine", et T. L. Vischer, of 1970.

The action of fluoride is explained, by a double mechanism, one of a biochemical nature and the other biological.

In the biochemical mechanism there is incorporation of the fluoride ion into the mineral structure of the bone, with a consequent increase in the dimensions of the hydroxyapatite cristal. This causes the hydroxyapatite to become less water-soluble and increases the binding force between the organic matrix and these cristals with a consequent improvement in the more mechanical properties of the bone structure. An increase in the crystallinity index has been determined experimentally by measurements using an infrared spectrometer.

In the biological mechanism on the other hand there is direct stimulation of the osteoblasts, which can be detected as an increase in their number and activity, and by transitory morphological changes in them, and therefore with the consequent new production of uncalcified bone matrix. The histomorphometric consequence of this succession in an increase in the volume of the trabeculae which can reach 20% in the first year of the treatment.

With reference to the biochemical mechanism it should be noted that the fluoride ion is rapidly captured by the bone tissue and incorpored into the mineral structure of the hydroxyapatite where it displaces the hydroxil group (—OH) forming fluorohydroxyapatite (FAP). Fluoride ions can displaces up to 25% of the hydroxyl radicals in the hydroxyapatite with a maximum saturation concentration in bone of 20,000 to 35,000 parts per million, equivalent to 40-70 mg of sodium fluoride (NaF) per gram of bone tissue.

This value however represents the theoretical maximum corresponding to chemical saturation of the bone.

The actual values which can be measured in the course of oral treatment or in the case of occupational fluorosis are obviously very much lower because of the state of equilibrium which is set up between the amount taken up, the amount eliminated by excretion from the kidneys, the amount captured by the bone and the amount released through the effect of the half-life of the fluorine in the bone, which is about two years.

This systemic or oral administration of the fluoride has the following disadvantages.

When the drugs is taken in high doses it can cause excessive accumulation throughout the skeleton, with consequent pathological fluorosis of the bone and toxic effects in some of the patient's organs which can make it necessary to reduce the dosage of the drug, and may also produce an unacceptable level of local accumulation at the site of the implant.

The object of the invention is at least to minimise the abovementioned disadvantages.

According to the present invention there is provided a two phase cement mixture which is particularly suitable for orthopaedic uses, characterised in that the solid phase comprises a polymer, polymetyl methacrylate $(-(C_5H_8O_2)_n-)$ 97% and a catalyst, benzoyl peroxide $(C_{14}H_{10}O_4)$ 3%, while the liquid phase comprises a monomer, monomethyl methacrylate $(C_5H_8O_2)$ 99.10%, an accelerator, N-N-dimethyl-p-toluidine $(C_9H_{13}N)$ 0.89% and a stabiliser, hydroquinone approximately 20 parts per million, the amonth of liquid phase required to react with a standard 40 g dose of solid phase being 14 ml, and in which the said powder polymer, having particles of a spherical shape only, consists of:

spheres of diameter up to 0.90 μm, in a percentage lying between 0.60 and 2.00%, spheres of diameter 0.91 μm to 3.70 μm, in a percentage lying between 0.80 and 2.00%, spheres of diameter 3.71 μm to 10.50 μm, in a percentage lying between 3.00 and 5.00%, spheres of diameter 10.51 μm to 25.00 μm, in a percentage lying between 15.00 and 19.00%, spheres of diameter 25.01 μm to 51.00 μm, in a percentage lying between 45.00 and 55.00%, spheres of diameter 51.01 μm to 87.00 μm, in a percentage lying between 22.00 and 28.00%, the total percentage polymer in the powder passing the 87.00 μm sieve being equal to 100%.

Preferably the powdered polymethyl methacrylate is in particles of sferical shape only consists of:

spheres of diameter up to 0.90 μm, in a percentage lying between 0.60 and 2.00%, spheres of diameter 0.91 μm to 3.70 μm, in a percentage lying between 0.80 and 2.00%, in which the spheres having a diameter which passes the 1.10 μm sieve represent at least 30% of the totality of the said spheres and the spheres having a diameter passing through the 2.20 μm sieve represent at least 97% of all the said spheres, spheres of diameter 3.71 μm to 10.50 μm, in a percentage lying between 3.00 and 5.00%, in which the spheres having a diameter passing through the 9.00 and 10.50 μm sieves represent at least 25 and 27% of all the said spheres, spheres of diameter 10.51 μm to 25.00 μm, in a percentage lying between 15.00 and 19.00%, in which the spheres having a diameter passing through the 21.00 and 25.00 μm sieves represent at least 21 and 29% of all the said spheres, spheres of diameter 25.01 μm to 51.00 μm, in a percentage lying between 45.00 and 55.00%, in which the spheres having a diameter passing through the 51.00 and 43.00 μm sieves represent at least 28% of all the said spheres, spheres of diameter 51.01 μm to 87.00 μm, in a percentage lying between 22.00 and 28.00%, in which the spheres having a diameter passing through the 61.00 and 73.00 μm sieves represent at least 50 and 33% of all the said spheres,
the total percentage polymer in the powder passing the 87.00 μm sieve being equal to 100%.

An amount of floride between 3.0 and 9.0% in the form of a fluoride salt which is capable of releasing fluoride ions F− gradually, making them available to the bone, is added to the said mixture.

Preferred fluoride salts are: sodium fluoride (NaF), ammonium fluoride ($NH_4F$), sodium monofluoride phosphate ($Na_2PO_3F$), sodium silicofluoride ($Na_2SiF_6$), tin fluoride ($SnF_2$), potassium fluoride (KF), magnesium fluoride ($MgF_2$), lithium fluoride (LiF), zinc fluoride ($ZnF_2$), potassium hexafluorophosphate ($KPF_6$), ammonium hexafluorophosphate ($NH_4PF_6$), sodium hexafluorosilicate ($Na_2SiF_6$).

The solid phase and fluoride salt may be marketed in separate packs or jointly in the same pack.

Research into the phenomenon of detachment has resulted in identification of the following factors which give rise to detachment:

the chronic inflammatory reaction set up by the remains of the materials used for the prosthesis, mechanical yieding of the cement and other materials used due to the considerable and cyclically variable loads to which the materials are subjected during daily use of the prosthesis, lesion of the bone tissue caused by direct contact with the acrylic resin during polymerization, due to the large amount of the heat released by the resin following an exothermic polymerisation reaction; as described in the literature the threshold of heat damage for biological structure is around 70° C., above this threshold structure are irreversibly denatured, biological reaction of the bone tissue of a self-destructive or catabolic nature caused by abnormal biomechanical stimuli due to load on the implanted prosthesis acting at the cement-bone interface.

When the abovementioned causes of detachment had been identified efforts were made to prevent or at least limit these phenomena through the development of a bone cement having better mechanical strength, a low heat of polymerisation, below the threshold for heat demage to biological structures, and associated with fluoride salts which can release fluoride ions locally in a sufficient and harmless concentration in a gradual way over a long period of the time.

The main advantage offered by the invention consists of the fact that as a result of precise selection of the particle size and shape of the particles forming the solid phase of the bone cement the amount of liquid monomer required to cause a complete dose of cement powder to react completely and thus to obtain accurate and homogeneous mixing is reduced dramatically in comparison with the amounts usually used.

Bearing in mind that the amount of heat produced in the polymerisation reaction is proportional to the amount of liquid, this reduction in the amount of the liquid produces a proportional decrease in the amount of heat released by the polymerisation reaction, which for a given mass of cement is reflected in a fall in the absolute polymerisation temperature.

This temperature in thus kept below 55° C. in comparison with the 70°/90° C. reached in the clinical use of known cements, without this having any adverse effect on the mechanical strength characteristics of the product.

A further advantage, again due to the reduction in the amount of liquid phase used to obtain the cement paste, arises from the fact that the probability of the risk of cardio-respiratory collapse in the patient following administration of the liquid monomer is reduced.

Another advantage, confirmed by experiments performed on samples of cement according to the invention in a laboratory working to British Standard ISO/DP 5833/1, is due to the improvement in the mechanical properties of the cement itself in comparison with the corresponding properties of known cements obtained in the same tests and shown in Table II.

Yet another advantage is brought about by the addition of fluorine, in the form of salt, directly into the bone cement. The administration of fluorine in situ, in contact with the bone which is to receive it, eliminating the disadvantages of systemic administration, in fact appreciably improves the availability of the fluorine to the bone, making it available for a longer period of time.

It is in fact known that the amount of release is associated with various factors such as: the size of the molecule of the additive, the temperature and hydration of the environment and the extent of the area of contact between the cement and the environment.

It has also been found that the amount of release is greater in the presence of:

little or no chemical bonding between the additive and the polymer forming the cement, small size of the additive molecule, high temperature, large area of contact between the polymer and the bone tissue, biological liquids in contact with the polymer.

In the light of these studies, and beyond the restricted field of application of antibiotics, it has been concluded that sodium fluoride is a particularly suitable substance for local release in an slow and controlled manner.

Sodium fluoride in fact has following properties:

it contains the greatest amount of fluoride per unit weight, the molecule is simple and of fairly small size, it is not possible for chemical bond to form between carbon atoms and fluoride ions, and therefore between the polymer and the added fluoride, the diffusion of the fluorine in ionic form from the cement to the external environment is due to contact erosion of the water surface in the environment which dissolve the sodium fluoride, extracting $Na^+$ and $F^-$, there is not evidence of the chemical bonding between the hydroxyapatite of the bone tissue and the polymethyl methacrylate of the cement, while on the other hand the fluoride ion has been shown to have marked tropism for this mineral structure and it is preferentially captured by it through the dispacement of the hydroxyl ($-OH^-$) groups.

In view of the fact that the percentage dry weight of fluorine present in bone tissue varies physiologically between the level 0.06 and 0.10% and that the safe therapeutic range lies between 021 and 04% it follows that dosing with fluoride salt should aim to keep the local $F^-$ concentraction within this range.

As a result the change in the mechanical strength properties of the cement following the addition of fluoride salts in a percentage adequate to achieve the abovementioned conditions is negligible, as has been demonstrated in the laboratory tests.

In fact the range of variation in strength properties (5–10%) lies well within the limits of the acceptable variation in the mean values for these properties, these variations beig due for example to the different compositions of the polymers, or the viscosity during the polymerisation stage or again the different techniques of preparation and cementing used.

Other advantages will appear in the course of the following detailed description of a number of embodiments of the invention described below by way of nonrestrictive examples of the invention.

With reference to the orthopaedic dose of cement required to attach a prosthesis to the hip the solid phase of the bone cement according to the invention consists of 40 g of powder having the following coposition:

| | | |
|---|---|---|
| polymetyl methacrylate | $(-(C_5H_8O_2)_n-)$ | 97% |
| benzoyl peroxide | $(C_{14}H_{10}O_4)$ | 3% |

The liquid phase on the other hand consists of 14 ml of the following composition:

| | | |
|---|---|---|
| monomethyl methacrylate | ($C_5H_8O_2$) | 99.10% |
| N—N-dimethyl-p-toluidine | ($C_9H_{13}N$) | 0.89% |
| hydroquinone | | ~20 ppm |

We provide a second example in which the bone cement contains a fluoride salt, and in this case the composition of the solid phase is as follows:

| | | |
|---|---|---|
| sodium fluoride | (NaF) | 5% |
| polymetyl methacrylate | (—($C_5H_8O_2$)$_n$—) | 92.3% |
| benzoyl peroxide | ($C_{14}H_{10}O_4$) | 2.7% |

The composition of the liquid phase on the other hand is identical to that in the previous example.

The experimental tests performed in the laboratory have considered the various types of the bone cement available commercially, in addition of course to the cement according to the invention.

The instruments used to obtain the data given below in the corresponding tables were:

for photographic documentation an OPTIPHOT-M microscope provided with a NICON MICROFLEX FX photographic system, for particle size documentation a SYMPATEX laser granulometer.

The types of orthopaedic cement powder used were as follows: sample No. 1 from the CMW 1 company, Sample No. 2 from the SYMPLEX company, sample No. 3 according to the invention, sample Nos. 4 and 5 obtained in the laboratory by varying the particle size of the powders.

From an investigation using the microscope and the laser granulometer and laboratory tests on standard 40 g doses of powder it was found that:

Sample No. 1 consisted morphologically of a powder comprising a few spheres, a certain number of spheroids of irregular shape, of dimensions similar to the said spheres, and amorphous powder.

22 ml of liquid monomer were required in orter to obtain a paste having a certain degree of worability.

From the point of view of mechanical strength properties the standard tests performed in accordance with British Standard BS 3531 (Part 7) demonstrated that this sample conformed to the values by the tests.

As far as particle size is concerned it should be noted that the percentage passing the 0.90 μm optical sieve was 3.10%, the 10.50 μm sieve 16.87%, the 103.00 μm sieve 100%. The calculated specific surface area was 0.127 m$^2$/cm$^3$.

Sample No. 2 from the morphologica point of view was in the form of a powder consisting of a number of spheres with amorphous powder, there being a complete lack of spheroids.

The amount of liquid monomer absorbed was 20 ml.

The mechanical strength properties of the said sample were in accordance with the values required by the standards mentioned.

From the particle size analysis data it was found that the percentage passing the 0.90 μm optical sieve was 2.38%, the 10.50 μm sieve 25.23%, the 103.00 μm sieve 100%.

The specific surface area was 0.122 m$^2$/cm$^3$.

Sample No. 3, which was an embodiment of this invention, appeared from the morphological point of view as a powder consisting essentially of perfectly spherical particles of various sizes, being absultely free of particles produced by grinding of the polymer.

The amount of liquid phase absorbed was 14 ml.

The mechanical strength properties of the sample of bone cement according to the invention were in accordance with the values required by the BS standards.

From the particle size analysis data it was found that the percentage passing the 0.90 μm sieve was 1.2%, the particle size classes of 2.60, 3.10 and 3.70 μm were lacking completely, the percentage passing the 10.50 μm sieve was 6.68%, while the percentage passing the 87.00 μm sieve was 100%. The specific surface area was 0.061 m$^2$/cm$^3$.

Sample No. 4 appeared from the morphological point of view as a powder consisting solely of spheres, amorphous powder and spheroids being completely lacking.

The amount of the liquid phase absorbed was 13 ml.

The mechanical strength properties of this sample reached the minima specified by the test.

From the particle size data will be seen that the particle size classes up to the 5.00 μm sieve are completely lacking, the percentage passing the 10.50 μm sieve was only 0.51%, while 100% passed the 103.00 μm sieve. The specific surface area was 0.022 m$^2$/cm$^3$.

Sample No. 5 appeared from the morphological point of view as a powder consisting solely of spheres, amorphous powder and spheroids thus being completely absent.

The amount of the liquid phase absorbed was 13 ml.

The mechanical strength properties of this sample did not reach the minima specified by the test.

From the particle size analysis data will be seen that the shape of the distribution in similar to that of sample No. 4, in fact the particle size classes up to the 4.30 μm sieve were completely missing, the percentage passing the 10.50 μm sieve was only 1.31%, while 100% passed the 103.00 μm sieve. The specific surface area was 0.025 m$^2$/cm$^3$.

For ease of the comparison the more significant data concerning the particle size analysis made on the five sample investigated are shown in Table I.

TABLE I

| | SAMPLE No. | | | | |
|---|---|---|---|---|---|
| | 1 | 2 | 3 | 4 | 5 |
| SIEVE | | | | | |
| from 0,90 μm | 3,40% | 2,38% | 1,13% | 0,00% | 0,00% |
| 0,91 ÷ 2.20 μm | 4,84% | 3,71% | 1,13% | 0,00% | 0,00% |
| 2,21 ÷ 3,70 μm | 1,92% | 2,71% | 0,03% | 0,00% | 0,00% |
| 3,71 ÷ 10,50 μm | 6,71% | 16,43% | 4,39% | 0,55% | 1,31% |
| 10,51 ÷ 25,0 μm | 15,85% | 24,00% | 17.64% | 4,75% | 9,32% |
| 25,01 ÷ 51,0 μm | 42,66% | 27,87% | 49,76% | 39,59% | 42,66% |
| 51.01 ÷ 73.0 μm | 20,09% | 16,88% | 22,10% | 38,13% | 34,85% |
| 73,01 ÷ 87,0 μm | 4,28% | 4,82% | 3,82% | 12,42% | 9,66% |
| over 87,01 μm | 0,26% | 1,21% | 0,00% | 4,55% | 2,20% |
| SPECIFIC SURF.AREA m$^2$/cm$^3$ | 0,12749 | 0,12246 | 0,05935 | 0,021894 | 0,02552 |
| MONOMER ABSORBED by one dose ml | 22 | 20 | 14 | 13 | 13 |

As mentioned earliesr all five types of cement were subjected to copression tests using test pieces prepared under the same environmental conditions and using an appropriate cylindrical press having a diameter of 25 mm and a height of 10 mm as specified in the British standard mentioned.

All the test pieces were prepared the day before the test and the test procedures were in accordance with the requirements of the standards specified.

In Table II below we show mean values for the compressive strength, each relating to 20 test pieces, obtained as the ratio of the yield strength to the cross-sectional area of the test piece.

TABLE II

| | SAMPLE No. | | | | |
|---|---|---|---|---|---|
| | 1 | 2 | 3 | 4 | 5 |
| COMPRESSIVE STRENGTH M Pa | 84,5 | 89.0 | 106,0 | 65,0 | 60.0 |
| MINIMUM COMPRESSIVE STRENGTH: 70,0 M Pa (according to standard BS 3531) | | | | | |

From a comparison of the above samples it is clear that a precise choice of the polymer powder which is to be used to obtain the bone cement should be made from the point of view of both morphology and particle size.

If in fact the choice falls, as in the case of the samples 1 and 2, on a type of powder consisting of a mixture of polymer in the form of spheres of various sizes mexed with amorphous powder and/or irregular spheroids, there will be two main consequences from such a choice:

(a) the powder will have to absorb an appreciable quantity of liquid monomer in order to attain standard workability.

(b) orthopaedic cements having mechanical strength properties greater than the limits imposed by BS acceptance standards will be obtained.

If on the other hand the choice falls on the type of powder consisting only of spheres of almost equal diameter, as in the case of samples 4 and 5, or which in any event do not respect certain proportions between the percentages passing the various optical sieves, the consequences from this choice will be as follow:

(a) the powder will absorb a minimum amount of liquid monomer in order to reach a given standard workability.

(b) orthopaedic cements with mechanical strength properties below the limits specified by BS acceptance standards will be obtained.

It will be seen therefore that in the first case advantages are derived from the satisfactory mechanical properties of the cement, but not all the disadvantages resulting from the presence of an excessive amount of liquid monomer, i.e. high polymerisation temperature and cardio-respiratory shoch, will not be eliminated.

In the second case however the disadvantages due to the excessive amount of liquid monomer are avoided but the mechanical strength properties are not sufficient to ensure that the artificial prosthesis implant will ultimately prove satisfactory.

In the case of sample 3, i.e. in the case of the cement according to the invention, the choice of a particular type of powder with the said morphological and particle size characteristics achieves both advantages together, both those resulting from the reduced amount of liquid monomer and those resulting from the optimum mechanical strength properties.

From what has been said so far it is clear that the selection of a polymer powder consisting of spheres only is only valid if attention is paid to both the particle sizes and the relative percentages of the various fractions passing through the sieve.

In fact the presence of a fraction of 1.13% passing through the 0.90 μm sieve has a very important part to play, that is to fill the empty spaces left by the larger particles when they are in contact. This makes it possible to obtain a more compact and therefore stronger cement which is therefore suitable for orthopaedic use.

If this fraction is larger, for example in excess of 2.00%, as in the case of sample 1 and 2, surface effects predominate and the amount af the liquid monomer would have to be increased in order that the entire paste should react, and in order to achieve the required degree of workability. This phenomenon is even more marked if the particles are no larger spherical and therefore have a high specific area.

If the said fraction is completely absent, as in the case of sample 4 and 5 the spaces between the larger particles will be filled by monomer only and the final result will be a friable cement unsuitable for orthopaedic use, despite the fact that the polymerisation temperature will lie within harmless limits.

We claim:

1. A two phase cement mixture which is particularly suitable for orthopaedic uses, comprising a solid powder phase and a liquid phase, wherein the solid phase comprises a polymer, polymethyl methacrylate ($-(C_5H_8O_2)_n-$) and a catalyst, benzoyl peroxide ($C_{14}H_{10}O_4$), while the liquid phase comprises a monomer, monomethyl methacrylate $C_5H_8O_2$, an accelerator, N-N-dimethyl-p-toluidine $C_9H_{13}N$ and a stabilizer, hydroquinone, characterized in that:

(a) the polymer consists of particles of spherical shape only;

(b) the spherical particles are present in proportions with diameters ranging up to 87 μm; and (c) particles having diameter up to 0.90 μm comprise between 0.6% and 2.0% of the polymer.

2. A two phase cement mixture as claimed in claim 1, in which the amount of liquid phase required to react with a standard 40 g dose of solid phase is 14 ml, and in which the polymer, having particles of a spherical shape only, consists of:

spheres of diameter up to 0.90 μm, in a percentage lying between 0.60 and 2.00%, spheres of diameter 0.91 μm to 3.70 μm, in a percentage lying between 0.80 and 2.00%, spheres of diameter 3.71 μm to 10.50 μm, in a percentage lying between 3.00 and 5.00%, spheres of diameter 10.51 to 25.00 μm, in a percentage lying between 15.00 and 19.00%, spheres of diameter 25.01 μm to 51.00 μm, in a percentage lying between 45.00 and 55.00%, spheres of diameter 51.01 μm to 87.00 μm, in a percentage lying between 22.00 and 28.00%, and the total percentage polymer in the powder equal or smaller in diameter than 87.00 μm being equal to 100%.

3. A two phase cement mixture as claimed in claim 1 in which an amount of floride between 3.0 and 9.0% in the form of a fluoride salt which is capable of releasing fluoride ions, $F^-$ gradually, making them available to bone tissue is added to the said mixture.

4. A two phase cement mixture as claimed in claim 3, in which at least one of the following salts are added to the solid phase in the proportions specified: sodium fluoride (NaF), ammonium fluoride ($NH_4F$), sodium monofluoride phosphate ($Na_2PO_3F$), sodium silicofluoride ($Na_2SiF_6$), tin fluoride ($SnF_2$), potassium fluoride (KF), magnesium fluoride ($MgF_2$), lithium fluoride (LiF), zinc fluoride ($ZnF_2$), potassium hexafluorophosphate ($KPF_6$), ammonium hexafluorophosphate ($NH_4PF_6$), sodium hexafluorosilicate ($Na_2SiF_6$).

5. A two phase cement mixture as claimed in claim 2, in which an amount of fluoride between 3.0 and 9.0% in the form of a fluoride salt which is capable of releasing fluoride ions $F^-$ gradually, making them available to the bone tissue, is added to the said mixture.

* * * * *